United States Patent [19]

Holton et al.

[11] Patent Number: 5,227,400
[45] Date of Patent: Jul. 13, 1993

[54] FURYL AND THIENYL SUBSTITUTED TAXANES AND PHARMACEUTICAL COMPOSITIONS CONTAINING THEM

[75] Inventors: Robert A. Holton; Hossain Nadizadeh; Ronald J. Beidiger, all of Tallahassee, Fla.

[73] Assignee: Florida State University, Tallahassee, Fla.

[21] Appl. No.: 862,819

[22] Filed: Apr. 3, 1992

Related U.S. Application Data

[63] Continuation-in-part of Ser. No. 763,805, Sep. 23, 1991, abandoned.

[51] Int. Cl.$^5$ .................. A61K 31/335; C07D 305/14
[52] U.S. Cl. .................. 514/444; 514/449; 514/471; 544/59; 544/146; 544/152; 544/379; 546/196; 546/212; 546/214; 548/525; 548/527; 549/60; 549/473; 549/510; 549/511
[58] Field of Search .................. 544/59, 146, 152, 379; 546/196, 212, 214; 548/525, 527; 549/60, 473, 510, 511; 514/444, 471, 449

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 4,942,184 | 7/1990 | Haugwitz et al. | 514/449 |
| 5,015,744 | 5/1991 | Holton | 549/510 |

FOREIGN PATENT DOCUMENTS

| | | |
|---|---|---|
| 253738 | 7/1987 | European Pat. Off. |
| 253739 | 7/1987 | European Pat. Off. |
| 336840 | 4/1989 | European Pat. Off. |
| 336841 | 4/1989 | European Pat. Off. |

OTHER PUBLICATIONS

Denis and Greene, "A Highly Efficient, Practical Approach to Natural Taxol", J. Am. Chem. Soc. 1988, 110, 5917–5919.

Holton et al., "A Synthesis of Taxusin", J. Am. Chem. Soc., 1988, 110, pp. 6558–6560.

Holton, "Synthesis of the Taxane Ring System", J. Am. Chem. Soc., 1984, 106, pp. 5731–5732.

Mukerjee et al., "β-Lactams: Retrospect and Prospect", Tetrahedron vol. 34, Report No. 52, pp. 1731–1767 (1978).

Wani et al., "Plant Antitumor Agents. VI. The Isolation and Structure of Taxol, a Novel Antileukemic and Antitumor Agent from *Taxus brevifolia*", J. Am. Chem. Soc. 93:9, May 5, 1971, pp. 2325–2327.

Primary Examiner—C. Warren Ivy
Assistant Examiner—Ba K. Trinh
Attorney, Agent, or Firm—Senniger, Powers, Leavitt & Roedel

[57] ABSTRACT

A taxane derivative of the formula

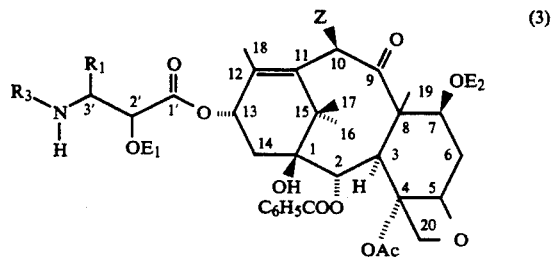

wherein

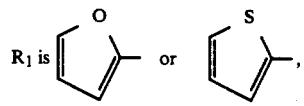

Z is —OT$_1$,

T$_1$ is hydrogen, hydroxyl protecting group, or —COT$_2$,

T$_2$ is H, C$_1$–C$_6$ alkyl, C$_1$–C$_6$ alkenyl, C$_1$–C$_6$ alkynyl or monocylic aryl, R$_3$ is benzoyl, substituted benzoyl or C$_1$–C$_6$ alkoxycarbonyl, Ac is acetyl, and E$_1$ and E$_2$ are independently selected from hydrogen and functional groups which increase the water solubility of the taxane derivative are useful as antitumor agents.

11 Claims, No Drawings

FURYL AND THIENYL SUBSTITUTED TAXANES AND PHARMACEUTICAL COMPOSITIONS CONTAINING THEM

REFERENCE TO RELATED APPLICATIONS

This application is a continuation-in-part application of U.S. Ser. No. 07/763,805, filed Sep. 23, 1991, now abandoned.

BACKGROUND OF THE INVENTION

The present invention is directed to novel taxanes which have utility as antileukemia and antitumor agents.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has a 2'R, 3'S configuration and the following structural formula:

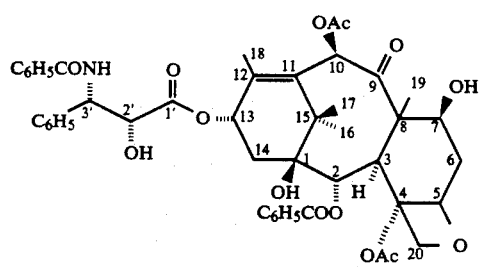

wherein Ac is acetyl. Because of this promising activity, taxol is currently undergoing clinical trials in both France and the United States.

Colin et al. reported in U.S. Pat. No. 4,814,470 that taxol derivatives having structural formula (2) below, have an activity significantly greater than that of taxol (1).

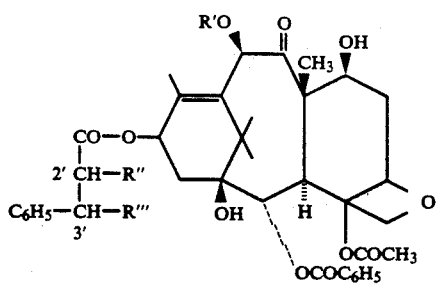

R' represents hydrogen or acetyl and one of R" and R'" represents hydroxy and the other represents tert-butoxycarbonylamino and their stereoisomeric forms, and mixtures thereof. The compound of formula (2) in which R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxane derivatives which are valuable antileukemia and antitumor agents.

Briefly, therefore, the present invention is directed to taxane derivatives of the formula:

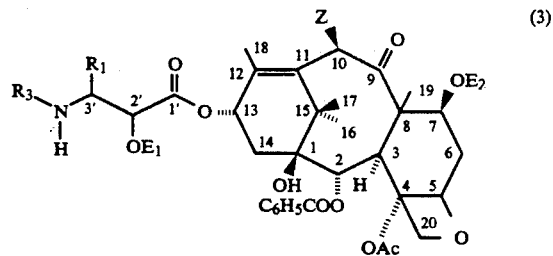

wherein

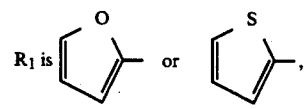

$Z$ is $-OT_1$, $T_1$ is hydrogen, hydroxyl protecting group, or $-COT_2$, $T_2$ is H, $C_1$-$C_6$ alkyl, $C_2$-$C_6$ alkenyl, $C_2$-$C_6$ alkynyl or monocylic aryl, $R_3$ benzoyl, substituted benzoyl or $C_1$-$C_6$ alkoxycarbonyl, Ac is acetyl, and $E_1$ and $E_2$ are independently selected from hydrogen, hydroxy protecting groups and functional groups which increase the water solubility of the taxane derivative.

Other objects and features of this invention will be in part apparent and in part pointed out hereinafter.

DETAILED DESCRIPTION OF THE PREFERRED EMBODIMENTS

In accordance with the present invention, it has been discovered that compounds having structural formula (3), in general, and structural formulas (4) and (5), in particular show remarkable properties, in vitro, and are valuable antileukemia and antitumor agents. Their biological activity has been determined in vitro, using tubulin assays according to the method of Parness et al., J. Cell Biology, 91: 479–487 (1981) and human cancer cell lines, and is comparable to that exhibited by taxol and taxotere.

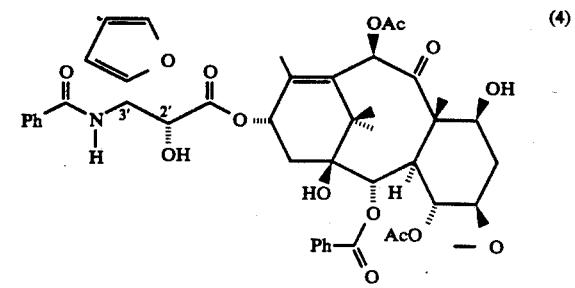

-continued

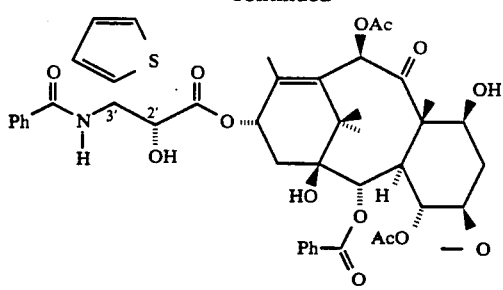

Taxanes having formulas (4) and (5) which have the 2'R, 3'S configuration may be obtained by reacting a β-lactam with metal alkoxides having the taxane tetracyclic nucleus and a C-13 metallic oxide substituent to form compounds having a β-amido ester substituent at C-13. The β-lactams have the following structural formula:

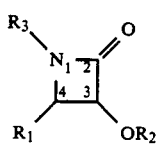

wherein

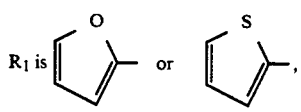

$R_2$ is a hydroxy protecting group,
$R_3$ is benzoyl, $C_1$-$C_6$ alkoxycarbonyl, or

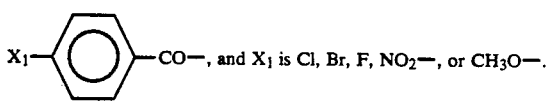

β-lactams (6) can be prepared from readily available starting materials, as is illustrated by the following reaction scheme:

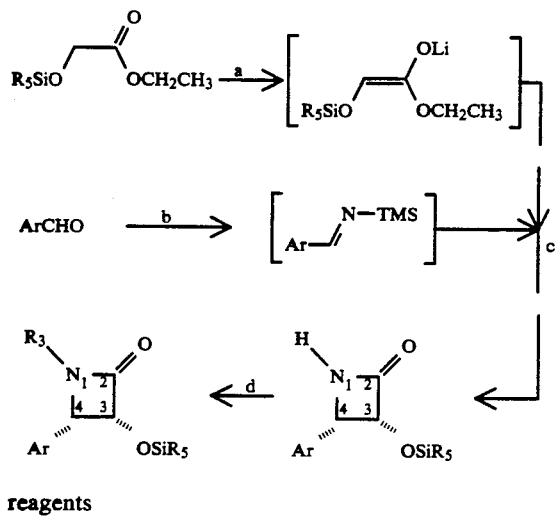

reagents (a) LDA, THF, $-78°$ C. to $-50°$ C.;
(b) LHMDS, THF, $-78°$ C. to $0°$ C.;
(c) THF, $-78°$ C. to $25°$ C. (2 h); and
(d) triethylamine and an acyl chloride

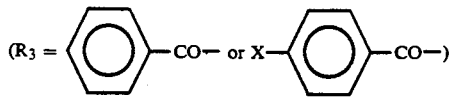

or alkyl chloroformate ($R_3$=alkoxycarbonyl).

The 3-hydroxyl protecting group shown in the above reaction scheme is —$SiR_5$ wherein $R_5$ is trialkyl or triaryl such as triethyl. The 3-hydroxyl may be protected with other standard protecting groups such as 1-ethoxyethyl, or 2,2,2-trichloroethoxymethyl. Additional hydroxy protecting groups and the synthesis thereof may be found in "Protective groups in Organic Synthesis" by T. W. Greene, John Wiley & Sons, 1981.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached has the advantage of being highly diastereoselective, thus permitting the use of a racemic mixture of side chain precursor.

The metal alkoxides having the taxane tetracylic nucleus and a C-13 metallic oxide substituent have the following structural formula:

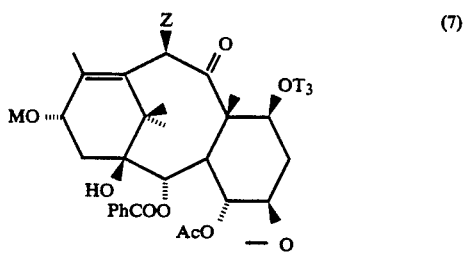

wherein Z is —$OT_1$; $T_1$ is hydrogen, hydroxyl protecting group, or —$COT_2$; $T_2$ is H, $C_1$-$C_6$ alkyl, $C_2$-$C_6$ alkenyl, $C_2$-$C_6$ alkynyl or monocylic aryl; $T_3$ is a hydroxy protecting group; and M is a metal, preferably selected from the group comprising Group IA, Group IIA and transition metals, and most preferably, Li, Mg, Na, K or Ti.

The metal alkoxides are prepared by reacting an alcohol having the taxane tetracylic nucleus and a C-13 hydroxyl group with an organometallic compound in a suitable solvent. Preferably, the alcohol is a protected baccatin III, in particular, 7-O-triethylsilyl baccatin III (which can be obtained as described by Greene, et al. in JACS 110: 5917 (1988) or by other routes) or 7,10-bis-O-triethylsilyl baccatin III.

As reported in Greene et al., 10-deacetyl baccatin III is converted to 7-O-triethylsily-10-deacetyl baccatin III according to the following reaction scheme:

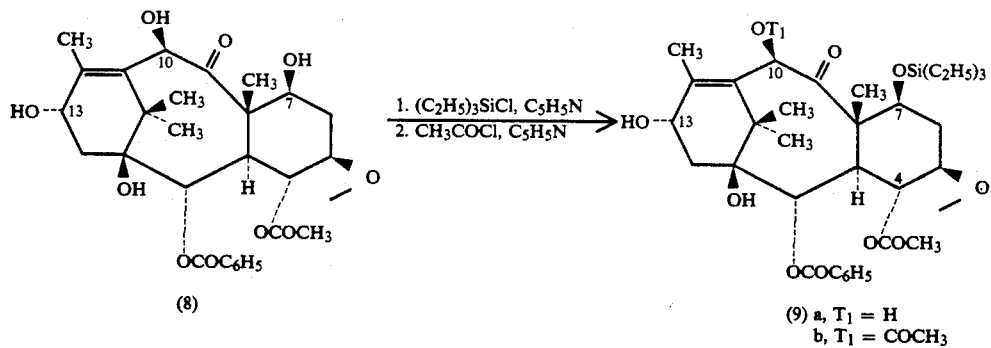

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (9a) as a reaction product in 84–86% yield after purification. The reaction product may then optionally be acetylated with 5 equivalents of $CH_3COCl$ and 25 mL of pyridine/mmol of 9a at 0° C. under an argon atmosphere for 48 hours to provide 86% yield of 7-O-triethylsily baccatin III (9b). Greene, et al. in JACS 110, 5917 at 5918 (1988).

The 7-O-triethylsily baccatin III (9b) is reacted with an organometallic compound such as n-butyllithium in a solvent such as tetrahydrofuran (THF), to form the metal alkoxide 13-O-lithium-7-O-triethylsilyl baccatin III (10) as shown in the following reaction scheme:

not to disturb the ester linkage or the taxane substituents.

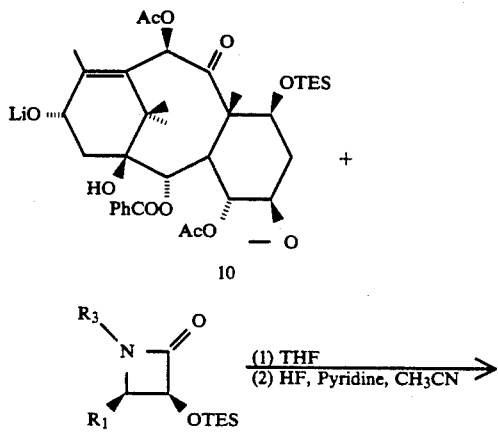

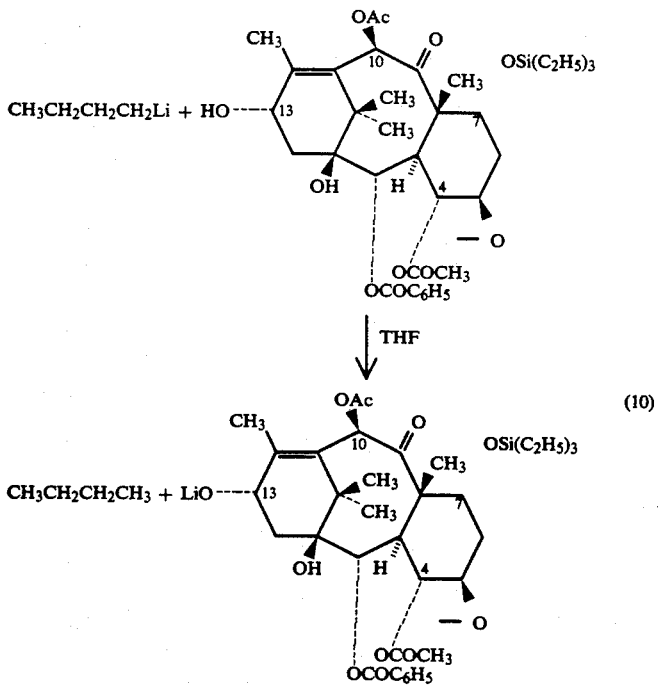

As shown in the following reaction scheme, 13-O-lithium-7-O-triethylsilyl baccatin III (10) reacts with β-lactam (6) in which $R_2$ is triethyl silyl to provide an intermediate in which the C-7 and C-2' hydroxyl groups are protected with a triethylsilyl group. The triethylsily groups are then hydrolyzed under mild conditions so as -continued

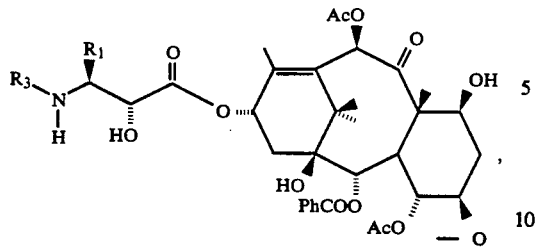

wherein

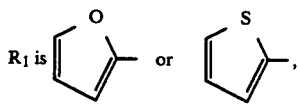

$R_3$ is benzoyl, $C_1$-$C_6$ alkoxycarbonyl, or

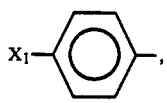

$X_1$ is Cl, Br, F, $NO_2$—, or $CH_3O$—.

Both the conversion of the alcohol to the metal alkoxide and the ultimate synthesis of the taxane derivative can take place in the same reaction vessel. Preferably, the β-lactam is added to the reaction vessel after formation therein of the metal alkoxide.

The present invention also provides pharmaceutical compositions containing a compound of formula (3), in general, and the compounds of formulas (4) and (5) in particular, in combination with one or more pharmaceutically acceptable, inert or physiologically active, diluents or adjuvants.

These compositions may be presented in any form appropriate for the administration route envisaged. The parental route, and especially the intravenous route, is the preferential route for administration.

The compositions according to the invention for parenteral administration may be aqueous or nonaqueous sterile solutions, suspensions or emulsions. Propylene glycol, vegetable oils, especially olive oil, and injectable organic esters, e.g. ethyl oleate, may be used as the solvent or the vehicle, These compositions may also contain adjuvants, especially wetting agents, emulsifiers or dispersants. The sterilization may be carried out in several ways, e.g. using a bacteriological filter, by incorporating sterilizing agents into the composition, by irradiation or by heating. They may also be in the form of sterile solid compositions which may be dissolved or dispersed in sterile water or any other injectable sterile medium.

The products of general formula (3) are more particularly used in the treatment of acute leukemias and solid tumors, at daily doses which are generally between 1 and 2 mg/kg by the intravenous (perfusion) route for an adult.

The water solubility of compounds of formula (3) may be improved by modification of the C2' and/or C7 substituents to incorporate appropriate functional groups, $E_1$ and $E_2$. For increased water solubility, $E_1$ and $E_2$ may independently be hydrogen and —COGCOR$^1$ wherein G is ethylene, propylene, CH=CH, 1,2-cyclohexane, or 1,2-phenylene, $R^1$=OH base, $NR^2R^3$, $OR^3$, $SR^3$, $OCH_2CONR^4R^5$, OH $R^2$=hydrogen, methyl $R^3$=$(CH_2)_nNR^6R^7$; $(CH_2)_nN^{\oplus}R^6R^7R^8X^{\ominus}$ n=1 to 3

$R^4$=hydrogen, lower alkyl containing 1 to 4 carbons $R^5$=hydrogen, lower alkyl containing 1 to 4 carbons, benzyl, hydroxyethyl, $CH_2CO_2H$, dimethylaminoethyl $R^6R^7$=lower alkyl containing 1 or 2 carbons, benzyl or $R^6$ and $R^7$ together with the nitrogen atom of $NR^6R^7$ form the following rings

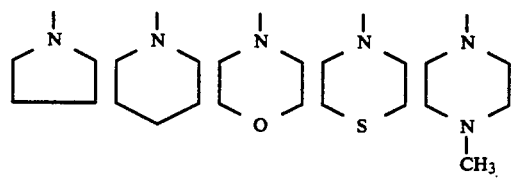

$R^8$=lower alkyl containing 1 or 2 carbons, benzyl
$X^{\ominus}$=halide
base=$NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $X_1$ or $X_2$ is —COGCOR$^1$ is set forth in Haugwitz U.S. Pat. No. 4,942,184 which is incorporated herein by reference.

The following examples illustrate the invention.

EXAMPLE 1

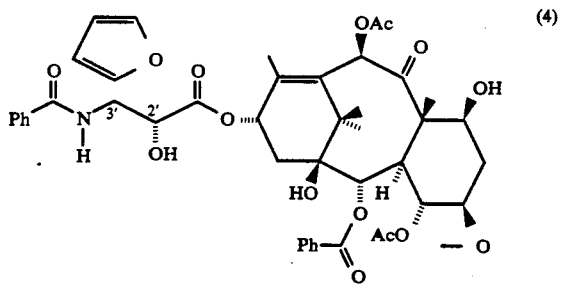

Preparation of 3'-desphenyl-3'-(2-furyl) taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-benzoyl-3-triethylsilyloxy-4-(2-furyl)azetidin-2-one (266 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 143 mg of a mixture containing (2'R,3'S)-2',7-(bis)triethylsilyl-3'-desphenyl-3'-(2-furyl) taxol and a small amount of the (2'S,3'R) isomer.

To a solution of 143 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 115 mg of material which was purified by flash chromatography to give 98 mg (81%) of 3'-desphenyl-3'-(2-furyl) taxol, which was recrystallized from methanol/water. m.p. 174°–176° C.; $[\alpha]_{Na}^{25}$ −47.8° (c 0.045, CHCl$_3$).

$^1$H NMR (CDCl$_3$, 300 MHz) δ 8.14 (d, J=7.0 Hz, 2H, benzoate ortho), 7.74 (m, 2H, aromatic), 7.51 (m, 7H, aromatic), 6.86 (d, J=9.2 Hz, 1H, NH), 6.40 (d, J=1.2 Hz, 2H, furyl), 6.29 (s, 1H, H10), 6.24 (dd, J=9.2, 9.2 Hz, 1H, H13), 5.89 (dd, J =9.2, 2.4 Hz, 1H, H3'), 5.69 (d, J=7.0 Hz, 1H, H2β), 4.96 (dd, J=9.5, 1.8 Hz, 1H, H5), 4.83 (d, J=2.4 Hz, 1H, H2'), 4.42 (dd, J=10.7, 6.7 Hz, 1H, H7), 4.31 (d, J=8.6 Hz, 1H, H20α), 4.20 (d, J=8.6 Hz, 1H, H20β), 3.83 (d, J=7.0 Hz, 1H, H3), 2.56 (m, 1H, H6α), 2.43 (s, 3H, 4Ac), 2.35 (m, 2H, H14), 2.24 (s, 3H, 10Ac), 1.89 (m, 1H, H6β), 1.87 (br, s, 3H, Me18), 1.87 (s, 1H, 10H), 1.69 (s, 3H, Me19), 1.25 (s, 3H, Me17), 1.15 (s, 3H, Me16).

EXAMPLE 2

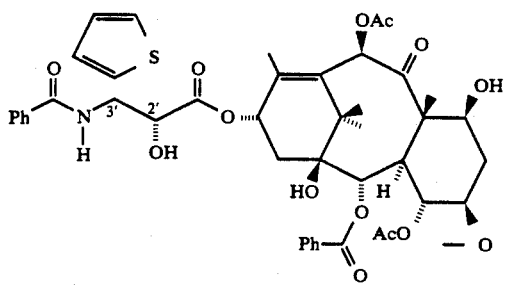

Preparation of 3'-Desphenyl-3'-(2-thienyl)taxol

To a solution of 7-triethysilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(4-benzoyl)-3-triethylsilyloxy-4-(2-thienyl)azetidin-2-one (277 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 169 mg of a mixture containing (2'R,3'S)-2',7-(bis)triethylsilyl-3'-desphenyl-3'-(2-thienyl) taxol and a small amount of the (2'S,3'R) isomer.

To a solution of 169 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 140 mg of material which was purified by flash chromatography to give 93 mg (76%) of 3'-desphenyl-3'-(2-thienyl) taxol, which was recrystallized from methanol/water. m.p. 173°–175° C.; $[\alpha]_{Na}^{25}$ −42.1° (c 0.515, CHCl$_3$).

$^1$H NMR (CDCl$_3$, 300 MHz) δ 8.14 (d, J=7.1 Hz, 2H, benzoate ortho), 7.72 (d, J=8.7 Hz, 2H, benzamide ortho), 7.65–7.35 (m, 6H, aromatic), 7.31 (dd, J=5.5, 1.1 Hz, 1H, thienyl), 7.19 (dd, J=3.9, 1.1 Hz, 1H, thienyl), 7.03 (dd, J=5.5, 3.9 Hz, 1H, thienyl), 6.96 (d, J=8.8 Hz, 1H, NH), 6.28 (s, 1H, H10), 6.24 (dd, J=8.8, 7.7 Hz, 1H, H13), 6.05 (dd, J=8.8, 1.7 Hz, 1H, H3'), 5.68 (d, J=7.1 Hz, 1H, H2), 4.95 (dd, J=9.3, 1.7 Hz, 1H, H5), 4.78 (d, J=2.2 Hz, 1H, H2'), 4.40 (dd, J=11.0, 6.6 Hz, 1H, H7), 4.31 (d, J=8.5 Hz, 1H, H20α), 4.20 (d, J=8.5 Hz, 1H, H20β), 3.81 (d, J=7.1 Hz, 1H, H3), 3.72 (br. s, 1H, 2'OH), 2.54 (m, 1H, H6α), 2.41 (s, 3H, 4Ac), 2.37 (m, 2H, H14α, H14β), 2.23 (s, 3H, 10Ac), 1.88 (m, 1H, H6α), 1.82 (br s, 3H, Me18), 1.68 (s, 3H, Me19), 1.23 (s, 3H, Me17), 1.14 (s, 3H, Me16).

EXAMPLE 3

Tubulin binding assays were performed using compounds (4) and (5) substantially as set forth in Parness et al., *J. Cell Biology* 91: 479–487 (1981) and compared to taxol and taxotere. The results are presented in Table 1.

TABLE 1

| Compound Name/Formula | Tubulin Assay | |
|---|---|---|
| | Init. Peak | Rel. Rate |
| 4 | 83 | |
| 5 | 75 | |
| Taxol | 100 | 98 |
| Taxotere | 100 | — |

EXAMPLE 4

IC$_{50}$ data were obtained in vitro on a human cancer cell line (HCT 116) which is available from the National Cancer Institute, and a multidrug resistant cell line (HCT/VM46), which is resistant to a variety of hydrophobic agents, including taxol. Cytotoxicity was assessed in HCT116 and HCT VM46 human colon carcinoma cells by XTT (2,3-bis(2-methoxy-4-nitro-5-sulfophenyl)-5-[(phenylamino)carbonyl]-2H-tetrazolium hydroxide assay (Scudiero et al, "Evaluation of a soluble tetrazolium/formazan assay for cell growth and drug sensitivity in culture using human and other tumor cell lines", *Cancer Res.* 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC$_{50}$ which is the drug concentration required to inhibit cell proliferation (i.e. absorbance at 450 nm) to 50% of that of untreated control cells. The results are presented in Table 2. Lower numbers indicate greater activity.

TABLE 2

| Compound Name/Formula | IC$_{50}$ | |
|---|---|---|
| | HCT 116 | HCT VM46 |
| 4 | 0.004 | 0.079 |
| 5 | 0.006 | 0.110 |
| Taxol | 0.004 | 0.536 |
| Taxotere | 0.007 | 0.246 |

In view of the above, it will be seen that the several objects of the invention are achieved.

As various changes could be made in the above compositions without departing from the scope of the invention, it is intended that all matter contained in the above description be interpreted as illustrative and not in a limiting sense.

What I claim is:

1. A taxane derivative of the formula

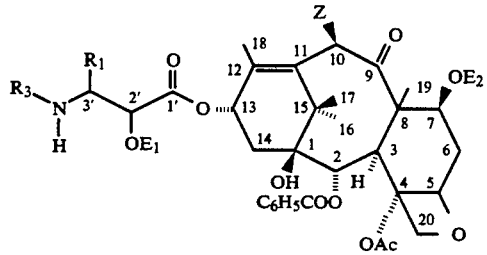
(3)

wherein

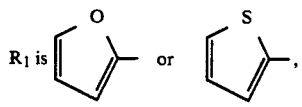

Z is —OT$_1$,

T$_1$ is hydrogen, hydroxyl protecting group, or —COT$_2$,

T$_2$ is H, C$_1$-C$_6$ alkyl, C$_2$-C$_6$ alkenyl, C$_2$-C$_6$ alkynyl or monocylic aryl, R$_3$ is benzoyl, substituted benzoyl or C$_1$-C$_6$ alkoxycarbonyl wherein the substitution is on the para-position of the benzoyl group and the substituent is selected from the group consisting of Cl, Br, F, NO$_2$— and CH$_3$O—, Ac is acetyl, E$_1$ and E$_2$ are independently hydrogen or —COG-COR$^1$ G is ethylene, propylene, CH=CH, 1,2-cyclohexane, or 1,2-phenylene, R$^1$=OH base, NR$^2$R$^3$, OR$^3$, SR$^3$, OCH$_2$CONR$^4$R$^5$, OH R$^2$=hydrogen, methyl R$^3$=(CH$_2$)$_n$NR$^6$R$^7$; (CH$_2$)$_n$N⊕R$^6$R$^7$R$^8$X⊖ n=1 to 3

R$^4$=hydrogen, lower alkyl containing 1 to 4 carbons

R$^5$=hydrogen, lower alkyl containing 1 to 4 carbons, benzyl, hydroxyethyl, CH$_2$CO$_2$H, dimethylaminoethyl R$^6$R$^7$=lower alkyl containing 1 to 2 carbons, benzyl or R$^6$ and R$^7$ together with the nitrogen atom of NR$^6$R$^7$ form the following rings

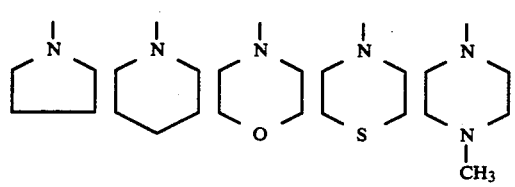

R$^8$=lower alkyl containing 1 to 2 carbons, benzyl

X⊖=halide and base=NH$_3$, (HOC$_2$H$_4$)$_3$N, N(CH$_3$)$_3$, CH$_3$N(C$_2$H$_4$OH)$_2$, NH$_2$(CH$_2$)$_6$NH$_2$, N-methylglucamine, NaOH, or KOH.

2. A taxane derivative of the formula

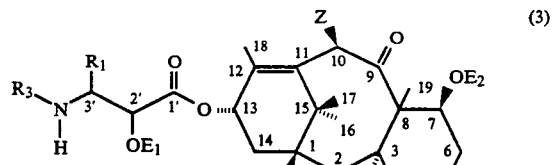
(3)

wherein

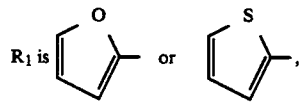

Z is —OT$_1$,

T$_1$ is hydrogen, hydroxyl protecting group, or —COT$_2$,

T$_2$ is H, C$_1$-C$_6$ alkyl, C$_2$-C$_6$ alkenyl, C$_2$-C$_6$ alkynyl or monocylic aryl, R$_3$ is benzoyl, substituted benzoyl or C$_1$-C$_6$ alkoxycarbonyl wherein the substitution is on the para-position of the benzoyl group and the substituent is selected from the group consisting of Cl, Br, F, NO$_2$— and CH$_3$O—, Ac is acetyl, and E$_1$ and E$_2$ are hydrogen.

3. The taxane of claim 2 wherein R$_1$ is

4. The taxane of claim 2 wherein R$_1$ is

and the taxane has the 2'R, 3'S configuration.

5. The taxane of claim 2 wherein R$_1$ is

6. The taxane of claim 2 wherein R$_1$ is

and the taxane has the 2'R, 3'S configuration.

7. A pharmaceutical composition which contains the taxane of claim 1 and one or more pharmacologically acceptable, inert or physiologically active diluents or adjuvants.

8. The composition of claim 7 wherein $R_1$ is

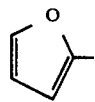

9. The composition of claim 7 wherein $R_1$ is

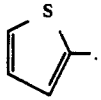

and the taxane has the 2'R, 3'S configuration.

10. The composition of claim 7 wherein $R_1$ is

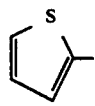

11. The composition of claim 7 wherein $R_1$ is

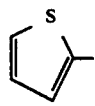

and the taxane has the 2'R, 3'S configuration.

* * * * *

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 2, lines 57-67, formula (4)

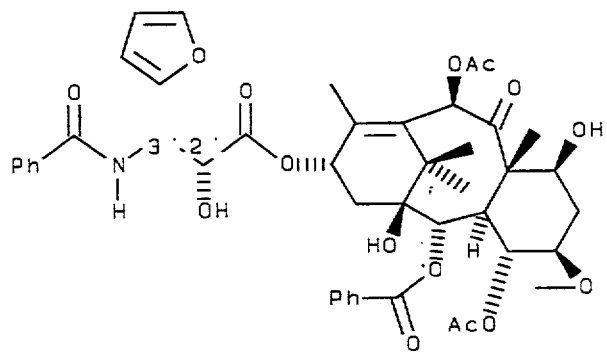

should read

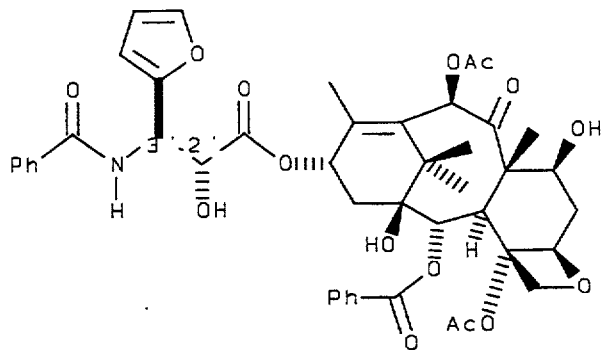

UNITED STATES PATENT AND TRADEMARK OFFICE
CERTIFICATE OF CORRECTION

PATENT NO. : 5,227,400

DATED : July 13, 1993

INVENTOR(S) : Robert A. Holton, Hossain Nadizadeh, Ronald J. Biediger

It is certified that error appears in the above-identified patent and that said Letters Patent is hereby corrected as shown below:

Column 3, lines 2-13, formula (5)

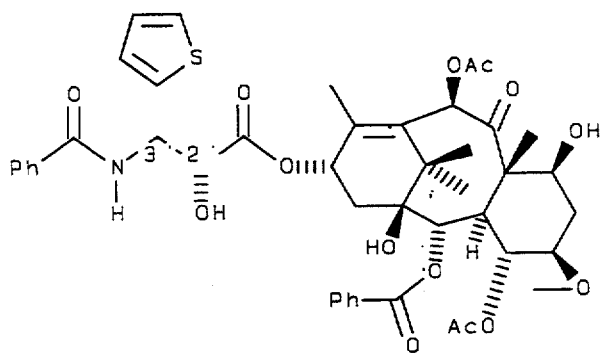

should read

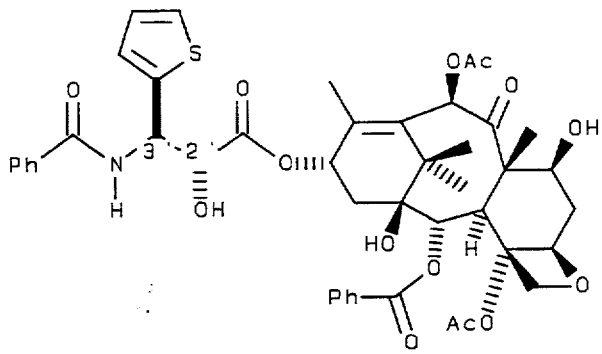

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 4, lines 37-47, formula (7)

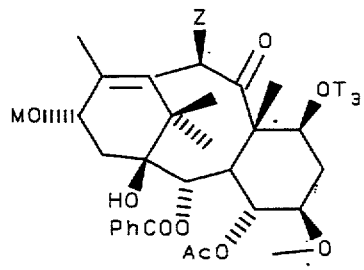

should read

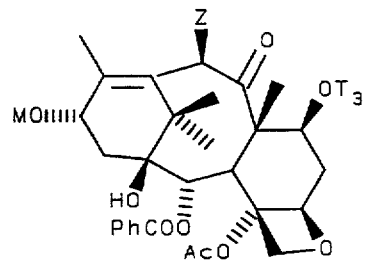

UNITED STATES PATENT AND TRADEMARK OFFICE
CERTIFICATE OF CORRECTION

PATENT NO. : 5,227,400  
DATED : July 13, 1993  
INVENTOR(S) : Robert A. Holton, Hossain Nadizadeh, Ronald J. Biediger Page 4 of 11

It is certified that error appears in the above-identified patent and that said Letters Patent is hereby corrected as shown below:

Columns 5 and 6, lines 1-15, formulas (8) and (9)

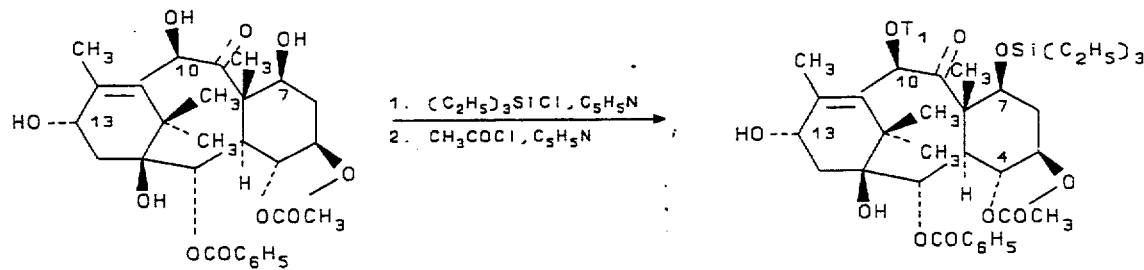

should read

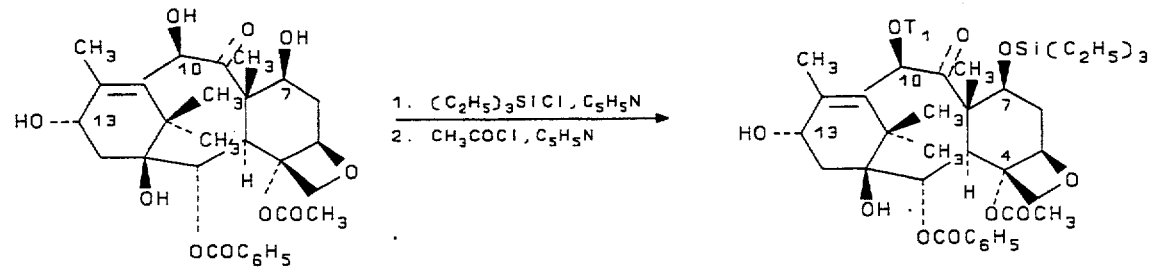

UNITED STATES PATENT AND TRADEMARK OFFICE
CERTIFICATE OF CORRECTION

PATENT NO. : 5,227,400

DATED : July 13, 1993

INVENTOR(S) : Robert A. Holton, Hossain Nadizadeh, Ronald J. Biediger

It is certified that error appears in the above-identified patent and that said Letters Patent is hereby corrected as shown below:

Column 5, lines 35-61, formula (10)

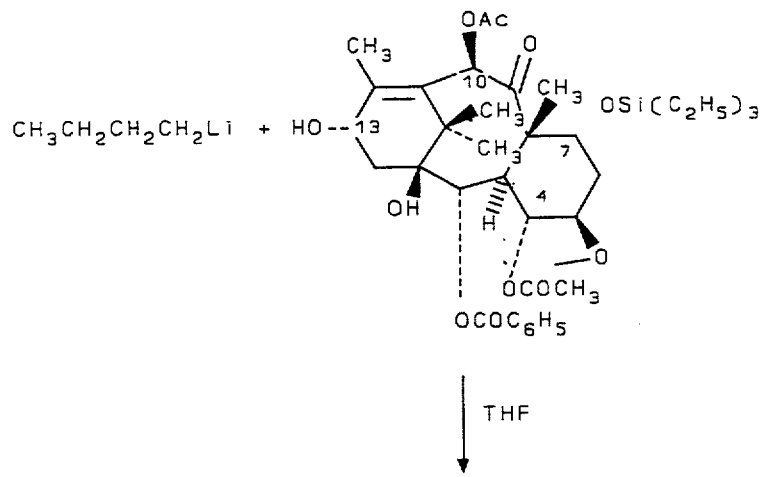

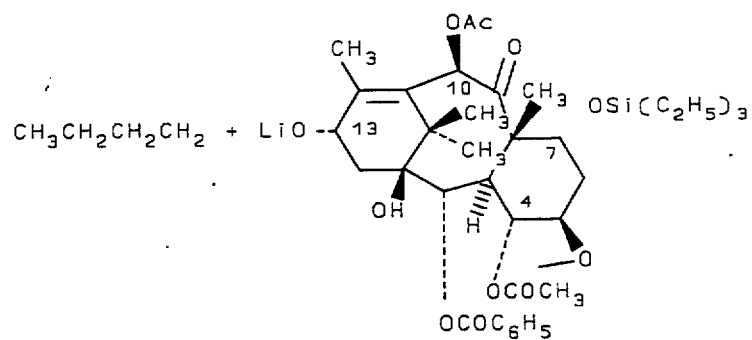

UNITED STATES PATENT AND TRADEMARK OFFICE
CERTIFICATE OF CORRECTION

PATENT NO. : 5,227,400  Page 6 of 11
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

should read

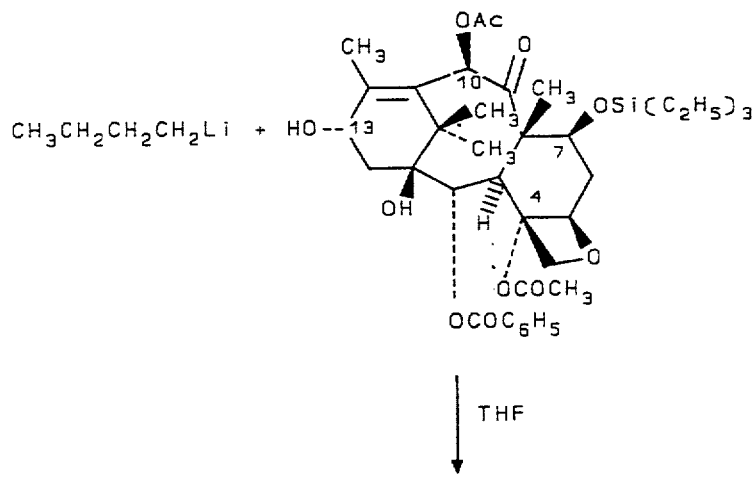

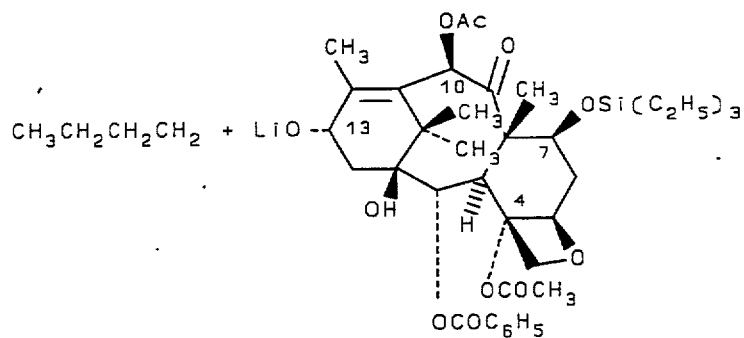

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 6, lines 20-30, formula (10)

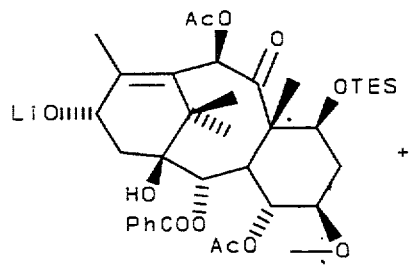

should read

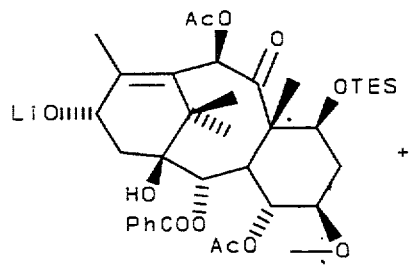

UNITED STATES PATENT AND TRADEMARK OFFICE
CERTIFICATE OF CORRECTION

PATENT NO. : 5,227,400

DATED : July 13, 1993

INVENTOR(S) : Robert A. Holton, Hossain Nadizadeh, Ronald J. Biediger

Page 8 of 11

It is certified that error appears in the above-identified patent and that said Letters Patent is hereby corrected as shown below:

Column 7, lines 2-11, the chemical formula

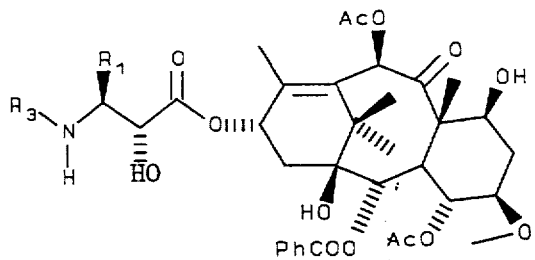

should read

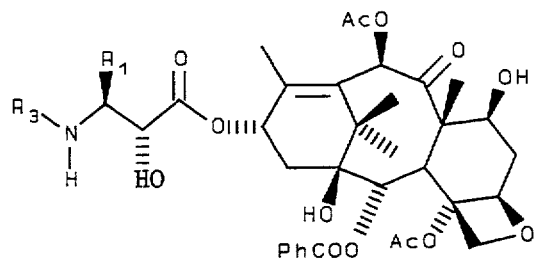

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 8, lines 38-48, formula (4)

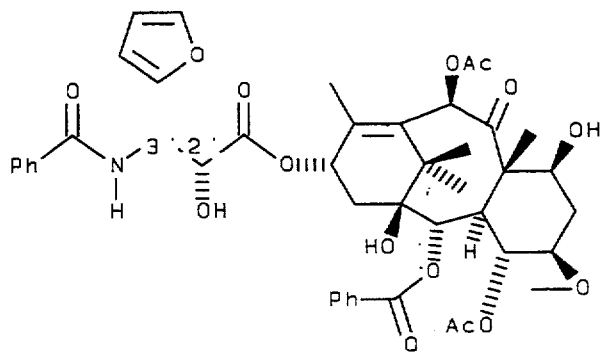

should read

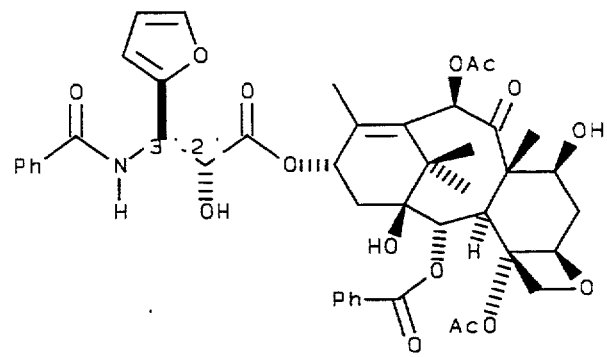

Column 9, line 8, "Na$^{25}$" should read ---$^{25}$Na---.

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 9, lines 25-35, formula (5)

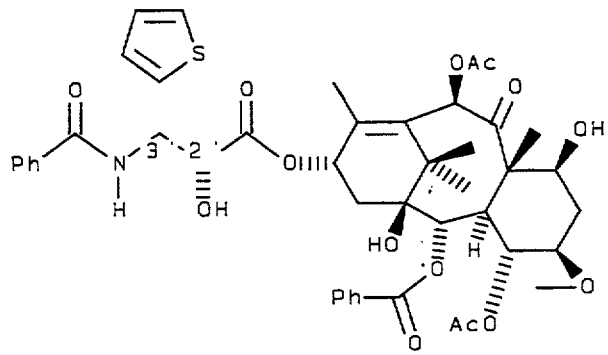

should read

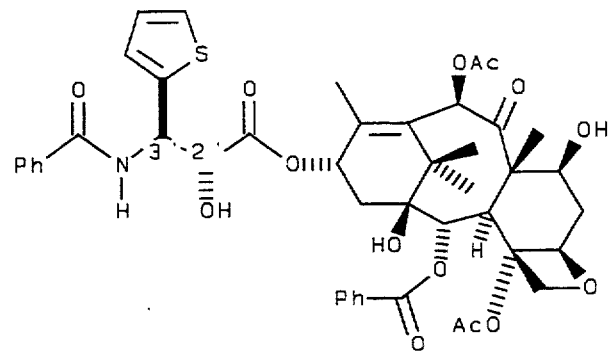

UNITED STATES PATENT AND TRADEMARK OFFICE
CERTIFICATE OF CORRECTION

PATENT NO. : 5,227,400
DATED : July 13, 1993
INVENTOR(S) : Robert A. Holton, Hossain Nadizadeh, Ronald J. Biediger It is certified that error appears in the above-identified patent and that said Letters Patent is hereby corrected as shown below:

Column 9, line 64, "$Na^{25}$" should read ---$^{25}Na$---.

Signed and Sealed this

Eighth Day of November, 1994

*Attest:*

BRUCE LEHMAN

*Attesting Officer*     *Commissioner of Patents and Trademarks*